United States Patent [19]

Russell

[11] Patent Number: 4,936,296
[45] Date of Patent: Jun. 26, 1990

[54] SPLINT DEVICE

[75] Inventor: Robert A. Russell, Annandale, Australia

[73] Assignee: Millar Mitchell & Co. Pty. Ltd., Double Bay, Australia

[21] Appl. No.: 191,951

[22] Filed: May 9, 1988

Related U.S. Application Data

[62] Division of Ser. No. 893,288, Aug. 5, 1986, Pat. No. 4,776,327.

[30] Foreign Application Priority Data

Aug. 9, 1985 [AU] Australia .................... 59208/86

[51] Int. Cl.$^5$ .............................................. A61F 5/04
[52] U.S. Cl. .................................. 128/87 R; 128/875; 128/88
[58] Field of Search .................... 128/78, 83, 85, 87 B, 128/87 R, 88, 89 R, 89 A, 90, 870, 875

[56] References Cited

U.S. PATENT DOCUMENTS

| | | | |
|---|---|---|---|
| 1,340,630 | 5/1920 | Maddox | 128/88 |
| 1,643,850 | 9/1927 | Jones | 128/88 |
| 2,312,523 | 3/1943 | Corbett | 128/85 |
| 2,362,866 | 11/1944 | Ulrich | 128/85 |
| 4,280,490 | 7/1981 | Santy | 128/87 R X |
| 4,718,665 | 1/1988 | Airy et al. | 128/88 X |

FOREIGN PATENT DOCUMENTS 49457 11/1889 Fed. Rep. of Germany ........ 128/88 UX Primary Examiner—Robert A. Hafer
Assistant Examiner—Sam Rimell
Attorney, Agent, or Firm—Finnegan, Henderson, Farabow, Garrett & Dunner

[57] ABSTRACT

A splint device for the spinal immobilization of a patient. The splint includes a central support portion and two pairs of laterally extending flexible wings adapted to extend, respectively, about the head and about the body of a patient and the central support portion is formed integrally with the wings from a synthetic plastics material and is concave on one side. The concavity includes a plurality of stiffening ribs adapted to render the central support portion substantially inflexible. The central support portion may be formed in two parts joined together by a lockable hinge such that the angle of inclination of a head part of the splint to the body part thereof may be selectively adjusted between 0° and 30°.

9 Claims, 6 Drawing Sheets

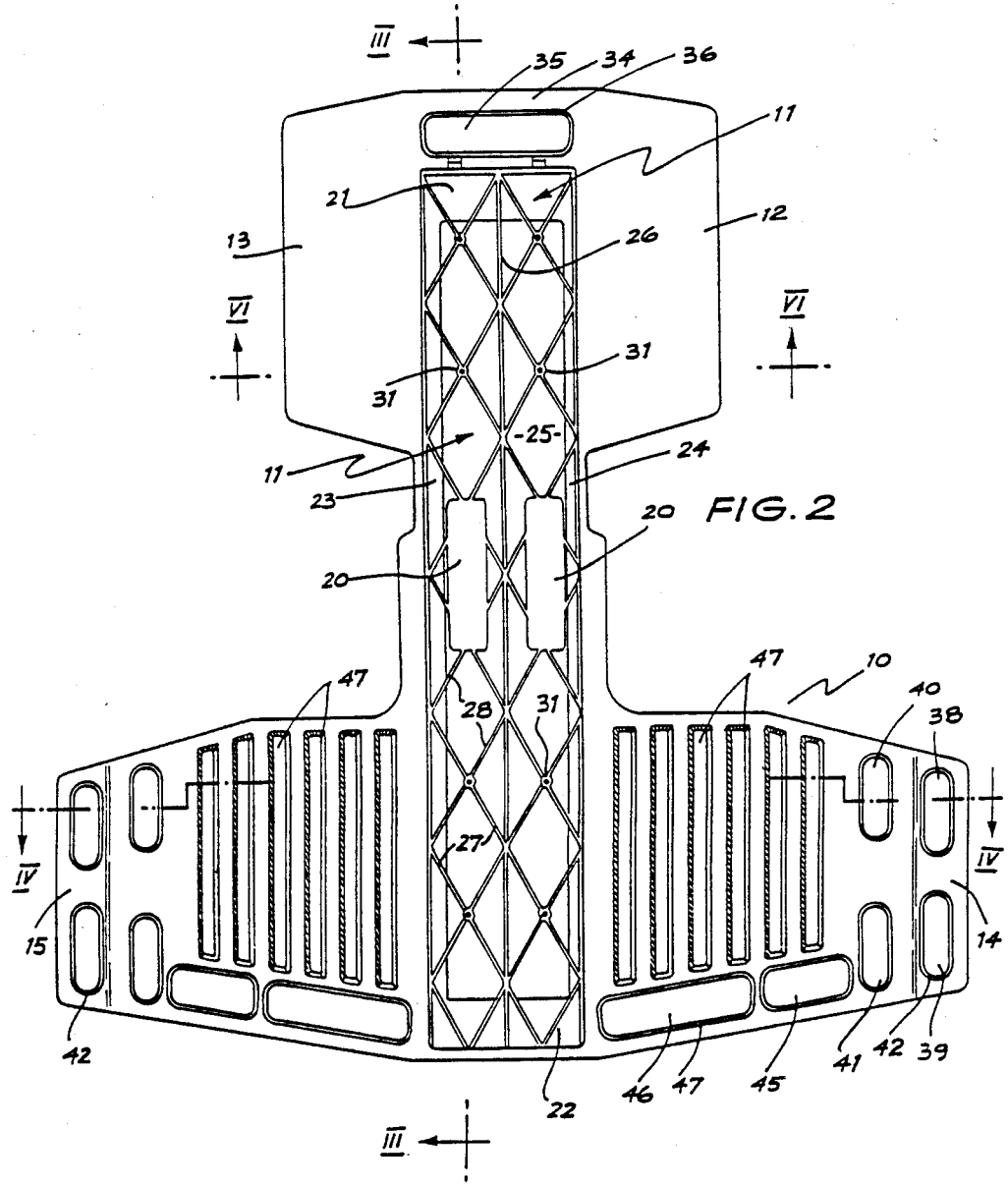

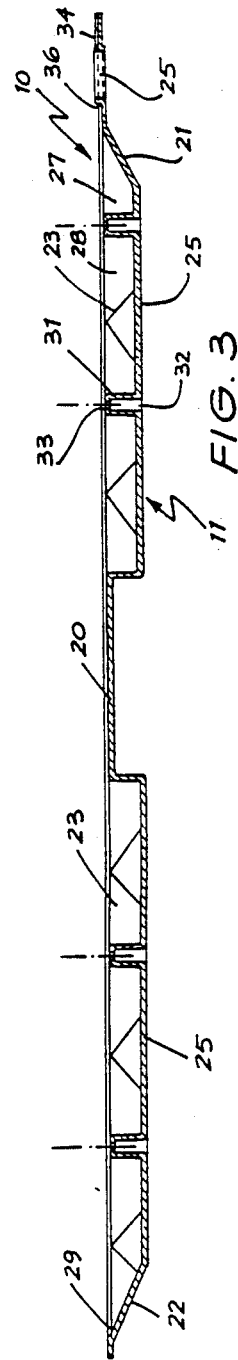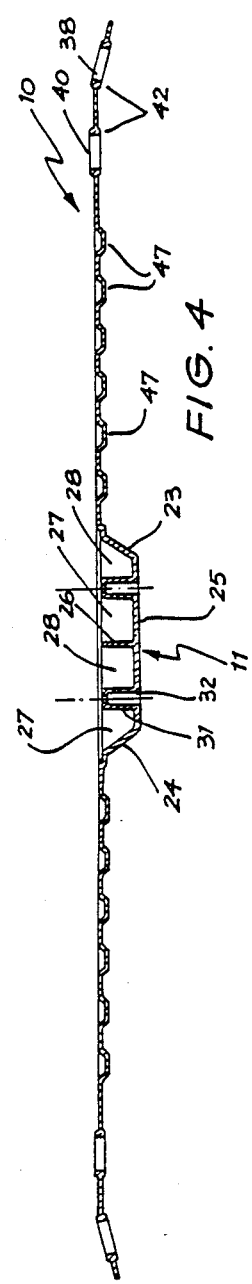

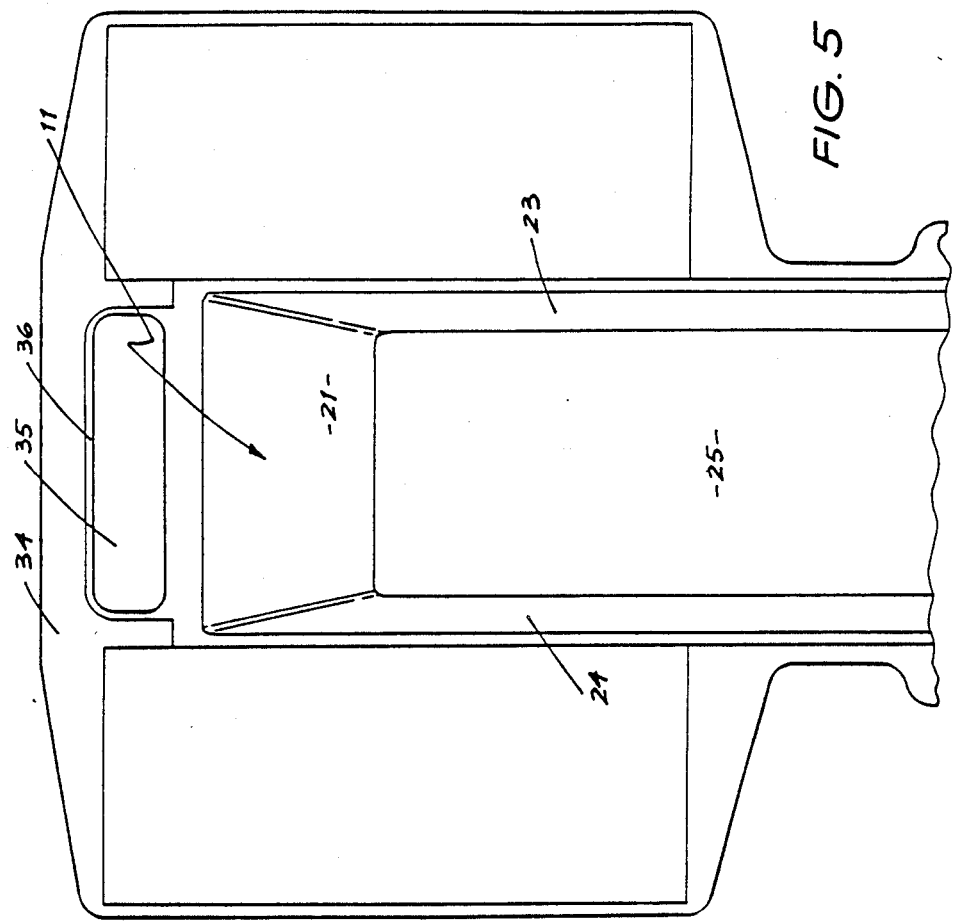

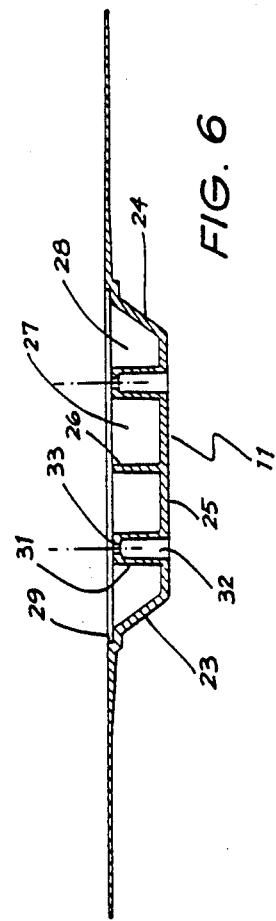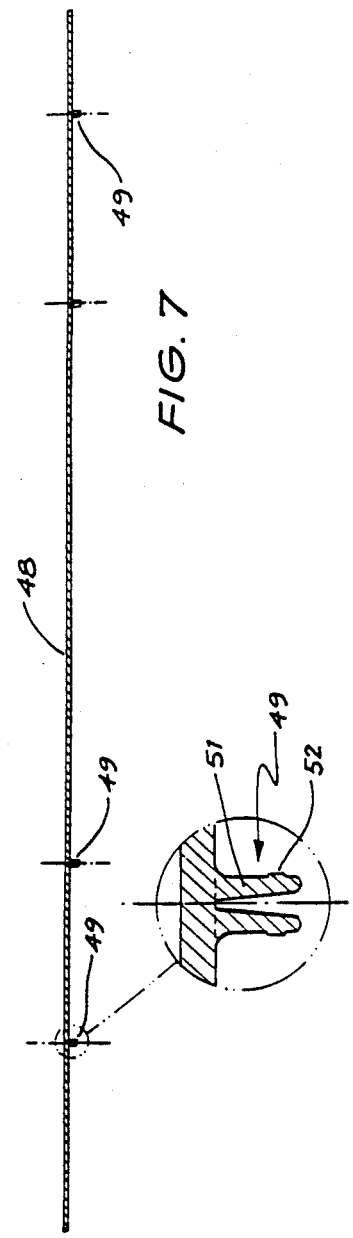

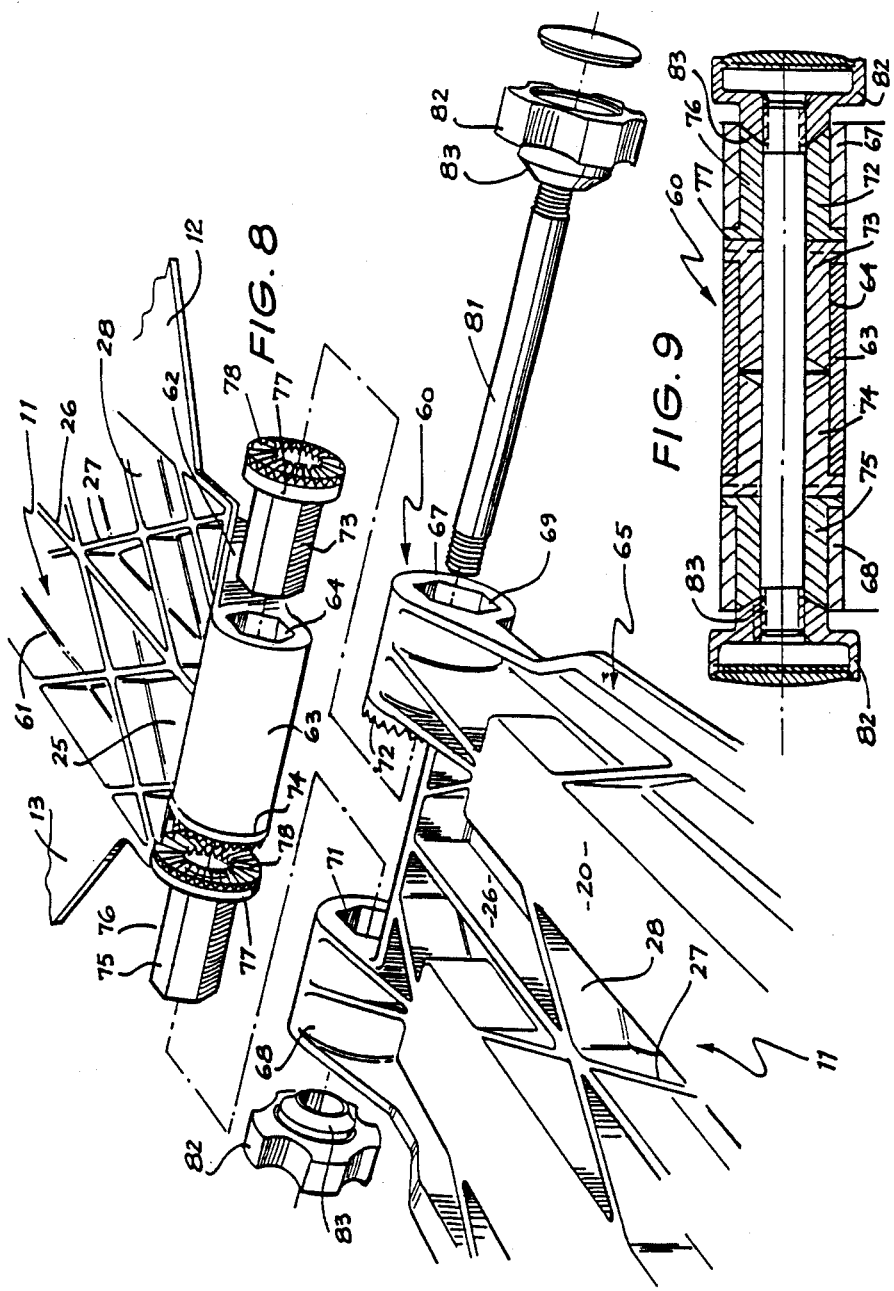

SPLINT DEVICE

This is a division of application Ser. No. 893,288, filed Aug. 5, 1986 now U.S. Pat. No. 4,776,327.

The present invention relates to a splint device for the spinal immobilization of a patient and more particularly to such a splint device wherein the majority of the splint is formed integrally from a synthetic plastics material.

Splints of the type to which the present invention relates are frequently used in emergency situations such as automobile accidents in which the patient has suffered injury, or suspected injury, to the back or neck areas. The handling of such injured patients requires special care in order to avoid further injury to the patient during the patient's extrication from the site of the accident and his transference to a hospital. Conventional stretchers do not meet the needs of such patients as it is often necessary to extricate the patient from a wrecked automobile, building site or some similar location where the patient cannot be disposed easily onto a stretcher. In these cases it is conventional to endeavour to immobilize the spinal column of the patient. Conventional splints of the type to which the present invention relates are made from a plurality of pieces such as wood and flexible fabric materials (see U.S. Pat. No. 4,211,218). It has not previously been considered possible to form such a splint from a single unitary plastic moulding due to the requirements that a central portion of the splint is required to be substantially rigid and inflexible while wings extending laterally from the central support portion are required to be flexible such that they may be wrapped around portions of the body of the patient to hold the spine of the patient against the central support portion of the splint.

In a first aspect the present invention consists in a splint device for the spinal immobilization of a patient, comprising a central support portion adapted to extend from the lumbar region to the head region of a patient, two pairs of laterally extending flexible wings attached to the side edges of the support portion, a first pair of the wings being adapted to extend about the head of a patient, and a second pair of the wings being adapted to extend about the thoracic and/or lumbar region of the patient, first engagement means adapted to retain the first pair of wings about the head of a patient and second engagement means adapted to retain the said second pair of wings about the thoracic and/or lumbar regions of a patient, the splint device being characterized in that the central support portion is formed integrally with the wings from a synthetic plastics material and has a cavity on one side and includes within the cavity a plurality of stiffening ribs adapted to render the central support portion substantially inflexible.

In a second aspect the present invention consists in a splint device for the spinal immobilization of a patient, comprising a central support portion adapted to extend from the lumbar region to the head region of a patient, two pairs of laterally extending flexible wings attached to the side edges of the support portion, a first pair of wings being adapted to extend about the head of a patient and a second pair of wings being adapted to extend about the thoracic and/or lumbar region of the patient, first engagement means adapted to retain the first pair of wings about the head of a patient and second engagement means adapted to retain the said second pair of wings about the thoracic and/or lumbar regions of a patient, the splint device being characterized in that the central support portion comprises a part connected to the first pair of wings and a part connected to the second pair of wings, these parts being connected together by hinge means which include locking means adapted to releasably retain the two parts together in at least a plurality of desired angular inclinations relative to one another which lie between 0° to 30°.

The stiffening ribs positioned within the cavity serve to give the central support portion rigidity and inflexibility sufficient to adequately support the spine of the patient from moving in a way which could damage the patient's spinal cord if the patient's vertebrae have been damaged. These stiffening ribs serve to mechanically rigidify the plastics material which has been selected specifically to give flexibility to the wings which are formed integrally with the central support portion. The central support portion itself, is preferably concave on the side proximal to the side which will come into contact with a patient in use and the integrally formed ribs, or at least some of them, preferably run diagonally of the central support portion. The use of at least some diagonal ribs in the cavity provides improved torsional rigidity as compared with ribs which only run longitudinally and/or transversely of the central support portion of the splint device. In a particularly preferred embodiment of the invention two sets of substantially parallel diagonal ribs are provided in the cavity, ribs of the respective sets intersecting. Such an array of intersecting diagonal ribs may be combined with one or more longitudinal and/or transverse ribs.

In a particularly preferred embodiment of the invention a closure panel is provided on the central support portion to cover the cavity and the integrally formed stiffening ribs contained therein. The closure panel is preferably so connected with the central support portion that its outer surface is flush with the outer surface of the central support portion or any other portion of the device with which it is contiguous. In this way the splint device may be given a smooth exterior shape such that it may readily be positioned about a patient even if it has to be slid between the patient and a car seat or the like on which the patient was positioned when the accident occurred.

The wings must have sufficient flexibility to allow them to be freely positioned about the patient. In one embodiment of the invention each wing of at least one pair of wings is formed with a plurality of spaced apart, substantially parallel and longitudinally extending, integral hinges. These hinges need to be quite numerous in order to provide the wings with the desired flexibility. In a more preferred embodiment of the invention the wings of at least one pair are each formed of a moulded sheet (formed integrally with the central support portion) of the synthetic plastics material and is of such a thickness and the synthetic plastics material is so selected that the wing is inherently flexible. It is particularly preferred that the thickness of the wing tapers, continuously or discontinuously, from a position adjacent the central support portion to a position adjacent the free end of that wing. It is particularly preferred that each wing tapers from a thickness of from 3 to 5mm adjacent the central support portion to a thickness of from 0.5 to 2.5mm adjacent the free end of that wing. It is also particularly preferred that the wings, and therefore the whole splint device, is formed of polypropylene.

The wings of at least one pair are, in a most preferred embodiment of this invention, formed of such a sheet of synthetic plastics material which tapers slightly towards its free end as has been described and which is formed with an array of longitudinally extending, substantially parallel, corrugations, each of which extends part way across the width of the wing but without making contact with the edge thereof. Each of these corrugations preferably extends through the full thickness of the wing. Each corrugation is preferably separated from the next adjacent corrugation by a planar portion of the wing which portion has a width of from 0.3 to 3.0 times the width of the corrugation. These corrugations provide to the wings a longitudinal stiffness without inhibiting the freedom with which the wing may be wrapped around the appropriate region of the patient's anatomy. This longitudinally stiffness is desirable to stop one wing "riding" up or down on the patient's body relative to the other wing to which it is connected by the respective one of the engagement means.

In a preferred embodiment of the invention the first engagement means comprise a pair of straps adapted to be passed around the forehead and chin respectively of a patient and connected at each end to one or other of the first pair of wings. The second engagement means preferably comprises straps adapted to pass around the legs and abdomen of a patient. The straps are preferably connected to the second wings by releasable clips or buckles or are formed in two parts each of which is connected to one of the second pair of wings, the strap parts being connectable together by releasable clips or buckles.

There are situations where a patient's anatomy is such, or where the patient's position after an accident is such, that it is not appropriate or desirable that the part of the central support portion in the region of the head of the patient be in axial alignment with the part of the central support portion in the thoracic or lumbar region of the patient. The second aspect of the present invention addresses this problem by providing a hinge between these parts of the central support portion. This hinge can preferably operate over a range of about 30° with the parts in alignment at one end of the range and out of alignment by the full 30° at the other end of the range. It is important that locking means are provided to releasably retain the two parts in substantially any desired relative angular relationship.

In a preferred embodiment of the invention the hinge comprises tubular members on each part adapted to be arranged in axial alignment such that they interdigitate with one another, the locking means comprising bolt means extending axially through the interdigitated tubular members and means on the bolt means to releasably clamp the tubular members together by axial pressure on the opposite end ones thereof.

Hereinafter described by way of example only, are preferred embodiments of the present invention described with reference to the accompanying drawings, in which:

FIG. 2 is a front elevational view of the splint of FIG. 1 without fastening means and with the cover plate removed;

FIG. 3 is a cross-sectional view along III—III of the splint according to FIG. 2;

FIG. 4 is a cross-sectional view along IV—IV of the splint according to FIG. 2;

FIG. 5 is a rear elevational view of the head portion of the splint according to FIG. 2;

FIG. 6 is a cross-sectional view along VI—VI of the splint according to FIG. 2,

FIG. 7 is a longitudinal sectional view through a cover plate for attachment to the splint of FIG. 2 showing an enlargement of a nipple for connection of the cover plate to the splint;

FIG. 8 is an exploded perspective view of a portion of a splint according to this invention showing a hinged connection between the head portion and the thoracic portion of the support portion thereof; and FIG. 9 is a cross-sectional view through the hinge of the embodiment of the invention depicted in FIG. 8.

Figure 1:
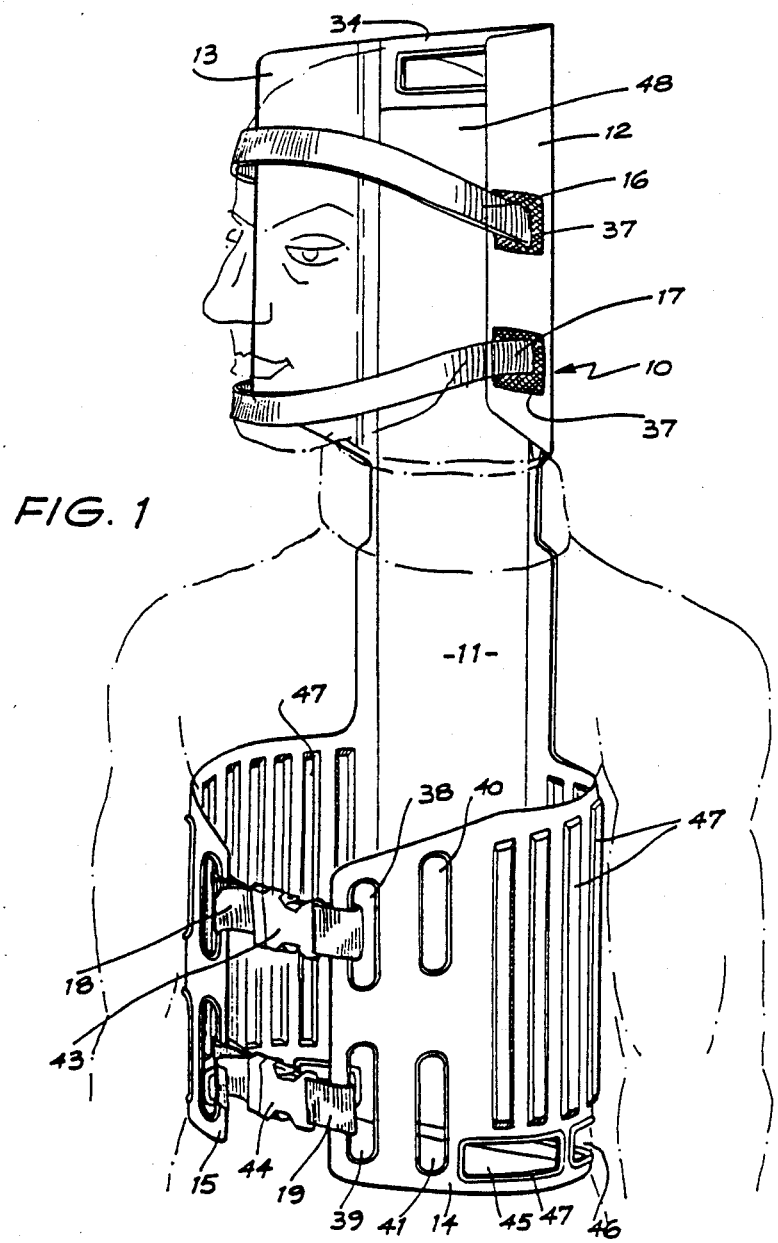
FIG. 1 is a perspective view of a splint according to the present invention in position on a patient.

The splint device 10 according to FIGS. 1 to 7 comprises a central support portion 11, a first pair of wings 12 and 13 adapted to extend about the head of a wearer, a second pair of wings 14 and 15 adapted to extend about the body of a wearer, a first pair of straps 16 and 17 adapted to hold wings 12 and 13 about the wearer's head and a second pair of straps 18 and 19 adapted to hold wings 14 and 15 about the wearer's body.

The central support portion 11, as is best seen in FIG. 2, is rectangular and concave, being recessed on its side proximal to the patient. The central support portion 11 comprises a pair of inclined end walls 21 and 22, a pair of inclined side walls 23 and 24, and a back wall 25. Within the recess formed by the end walls 21 and 22, the side walls 23 and 24, and the back wall 25 are a plurality of stiffening ribs. One stiffening rib 26 extends longitudinally of the recess; one set of ribs 27 extend diagonally across the recess in one direction; and a second set of ribs 28 extend diagonally across the recess in a direction transverse to the set of ribs 27 such that there is a minimum included angle therebetween of approximately 60°. Each of the ribs 26, 27 and 28 is formed integrally with the central support portion and extends from the back wall 25 up to a level flush with a ledge 29 which surrounds the recess. At the point of intersection of some of the ribs 27 and 28 an enlarged boss 31 is formed. Each boss is formed with an axially extending bore 32. At it upper end each bore 32 is constricted by an annular, inwardly directed flange 33.

The back wall 25 is itself provided with two indentations 20, one spaced equidistantly on each side of rib 26 midway between the zones over which the wings 12 and 13 join the central support section 11. The indentations 20 are of such a depth that the back wall 25 is, over the areas of the indentations 20, flush with the free edges of the ribs 26, 27 and 28 and the ledge 29. These indentations 20 add further to the stiffening of the central support portion provided by ribs 26, 27 and 28.

The central support portion 11 includes a substantially planar extension 34 at its head end in which is formed an aperture 35 by which the splint 10 may be carried. The aperture 35 is strengthened by a peripheral rib 36.

The first pair of wings 12 are substantially planar having a thickness adjacent to the central support portion 11 of 3mm and tapers to 1.5mm adjacent its free edge. The outer face of each wing is provided with two pads 37 of a "hook and loop" fastener material such as that sold under the trade mark "VELCRO". Each of the straps 16 and 17 is provided on its inside surface adjacent its ends with a complimentary pad (not shown) of the fastener material.

The second wings 14 and 15 are each provided adjacent their free ends with two pairs of apertures 38, 39, 40 and 41, each of which is surrounded by a stiffening rib 42. The strap 18 is adapted to be connected at its ends to a respective pair of apertures 38, or, in the case of a patient of slight build, to the apertures 40. Similarly, strap 19 is adapted to be connected at its ends to apertures 39 and 41. Each of the straps 18 and 19 is provided with a buckle, 43 and 44 respectively, allowing the strap to be rejoinably broken intermediate their respective ends.

The lower edge of each of the wings 14 and 15 is provided with a pair of apertures 45 and 46 which are each surrounded by a strengthening rib 47. These apertures 45 and 46 are adapted to be connected to straps encircling the patient's thighs if that is required for the safe handling of the patient.

Each of the wings 14 and 15 is provided with a plurality of elongate, substantially parallel corrugations 47. Each corrugation 47 stops short of the free edge of the wing 14 or 15 and serves to provide longitudinal stiffening to the wing which not restricting its flexibility as it is wrapped around the body of a patient. The wings 14 and 15 taper in thickness from about 5mm adjacent the central support portion 11 to about 2.5mm adjacent its free edge.

A cover plate 48 is provided to cover over the recess in the central support portion 11. The plate 48 is provided on one face with detent devices 49 made up of a pair of divergent fingers 51 each of which is provided adjacent its free end with a radially outwardly projecting protuberance 52. The detent devices 49 are adapted to project into the bores 32 in bosses 31 of the central support portion 11. The protruberances 52 on fingers 51 engage behind respective flanges 33 to hold the plate 48 in place on the central support portion 11. The free edges of plate 48 nest into the ledge 29 surrounding the recess in the central support portion 11 and the face of the plate 48 carrying the detent devices 49 lies flush with the free edges of the ribs 26, 27 and 28 and the back wall 25 in the region of indentations 20.

The central support portion 11 and wings 12, 13, 14 and 15 are formed integrally in a single moulding from polypropylene which is by its nature reasonably flexible. By providing the central support portion 11 with a recess containing the array of ribs 26, 27 and 28 the central support portion 11 is rendered sufficiently stiff to allow a patient's back to be immobilized while the wings retain the resilience and flexibility to be wrapped around a patient. The fact that the whole splint 10 is formed of essentially X-ray transparent materials allows a patient to be examined by X-rays without being removed from the splint.

The second aspect of the invention will now be described with reference to FIGS. 8 and 9. Similar parts of the splint 10 of this embodiment will receive the same numbers as they received in the description relating to FIGS. 1 to 7. In all respects except the provision of a hinge the splint 10 is identical with the splint 10 earlier described and for this reason the whole splint 10 is not described.

The hinge 60 is provided in the central support portion 11 between the indentations 20 and the start of the wings 12 and 13. The head part 61 of central support portion is provided with an end wall 62 and projecting from the end wall is a transversely extending tube 63 having a hexagonal bore 64. The tube 63 has its axis parallel to the plane of the back wall 25 and at right angles to the axis of the central support portion 11. The tube 63 is centrally disposed on wall 62 and is substantially shorter than it.

The body part 65 of the central support portion is provided with an end wall 66 from which extend a pair of spaced apart transversely extending tubes 67 and 68 each of which has a hexagonal bore 69 and 71 respectively.

The hinge includes four tubular locking pieces 72, 73, 74 and 75 formed of structural plastics material such as nylon. Each of the locking pieces 72, 73, 74 and 75 includes a hexagonal body part 76 and a flange 77 extending radially from one end of the body part. The face of each flange 77 distal to the body part 76 includes a plurality of radially directed teeth 78. A circular section bore 79 extends longitudinally through each of the locking pieces 72, 73, 74 and 75.

The locking piece 72 is positioned within bore 69 of tube 67 with its flange 77 facing inwardly and similarly locking piece 75 is positioned within bore 71 of tube 68. Locking pieces 73 and 74 are positioned within opposite ends of bore 64 in tube 63 with the flanges 77 facing outwardly.

When assembled the teeth 78 of respective pairs of locking pieces 72 and 73 and 74 and 75 interdigitate. A rod 81 which is threaded at each end extends through respective bores 79 in locking pieces 72, 73, 74 and 75. A wing nut 82 is threadedly engaged with each end of rod 81. Each wing nut 82 includes a frusto-conical face 83 surrounding bolt 81 which engages with a corresponding frusto-conical face surrounding the bore 79 of the locking pieces 72 and 75.

In use, when it is desired to change the relative angular inclination between the head part 61 and the body part 65 of the central support portion 11 the wing nuts 82 are loosened to enable the locking parts 73 and 74 to rotate relative to locking parts 72 and 75 as the head part 61 and body part 65 are rotated relative to one another. When the desired angular inclination has been achieved the wing nuts 82 are again tightened forcing flanges 77 of locking parts 72 and 73 and 74 and 75 together such that their interdigitating teeth 78 prevent further relative rotation between head part 61 and body part 65.

The positioning of tubes 63, 67 and 68 on the head part 61 and body part 65 is such that the parts 61 and 65 may rotate relative to one another between a position in which they are in axial alignment to a position in which they are 30° out of alignment.

I claim:

1. A splint device for the spinal immobilization of a patient, comprising a central support portion adapted to extend from the lumbar region to the head region of a patient, first and second pairs of laterally extending wings attached to side edges of the central support portion, said first pair of wings adapted to extend about the head of the patient and said second pair of wings being adapted to extend about at least one of the thoracic and lumbar regions of the patient, first engagement means adapted to retain the first pair of wings about the head of a patient and second engagement means adapted to retain the said second pair of wings about at least one of the thoracic and lumbar regions of the patient, the splint device being characterized in that the central support portion includes a part connected to the first pair of wings and a part connected to the second pair of wings, these parts being connected together by hinge means, which include locking means adapted to releasably retain the parts together in any desired angular inclination relative to one another of from 0° to 30°, with the attached pairs of wings of at least one of the central support portion parts including longitudinal stiffening means for supporting the patient in the longitudinal direction while permitting the wings to wrap around the patient.

2. A splint device as claimed in claim 1, in which the hinge comprises tubular members on each said part adapted to be arranged in axial alignment to interdigitate with one another, the locking means comprising bolt means extending axially through the interdigitated tubular members held together by axial pressure on the opposite end ones thereof.

3. A splint device as claimed in claim 2, in which a closure panel is connected to the central support portion with an outer surface of said closure panel flush with an outer surface of the central support portion or any other portion of the splint device with which the closure panel is contiguous.

4. A splint device for the spinal immobilization of a patient, comprising a central support portion adapted to extend from the lumbar region to the head region of a patient, first and second pairs of laterally extending flexible wings attached to side edges of the central support portion, said first pair of wings being adapted to extend about the head of a patient and said second pair of wings being adapted to extend about at least one of the thoracic and lumbar regions of the patient, first engagement means adapted to retain the first pair of wings about the head of a patient and second engagement means adapted to retain the said second pair of wings about at least one of the thoracic and lumbar regions of the patient, the splint device being characterized in that the central support portion includes a part connected to the first pair of wings and a part connected to the second pair of wings, these parts being connected together by hinge means, said hinge means comprising tubular members on each said part adapted to be arranged in axial alignment to interdigitate with one another, each of said tubular members having a non-circular internal bore in which is positioned at least one sleeve having a flanged end and an external shape corresponding to the bore of the tubular members such that the sleeve cannot rotate therein, the flanged end of adjacent sleeves being adapted to be engaged upon the imposition of axial pressure on ends of said tubular members, and said hinge further including locking means adapted to releasably retain each said part in any desired angular inclination relative to one another of from 0° to 30°, said locking means comprising bolt means extending axially through the interdigitated tubular members and means for producing axial pressure on opposite ends of said bolt means, 5. A splint device as claimed in claim 4, in which a free end face of each flanged end is castellated.

6. A splint device as claimed in any one of claims 4 or 5, in which at least one end of the bolt means is threaded and carries a correspondingly threaded nut the rotation of which relative to the bolt may serve to releasably clamp the tubular members together.

7. A splint device as claimed in any one of claims 4 or 5, in which at least one end of the bolt means is threaded and carries a correspondingly threaded nut for rotation relative to the bolt to releasably clamp the tubular members together.

8. A splint device as claimed in claim 4, in which the free end face of each flange is castellated.

9. A splint device for the spinal immobilization of a patient, comprising a generally rigid central support portion adapted to extend from the lumbar region to the head region adjacent the spline of a patient, first and second pairs of laterally extending flexible wings attached to side edges of the support portion, said first pair of the wings being adapted to extend about the head of a patient, and said second pair of the wings being adapted to extend about at least one of the thoracic and lumbar regions of the patient, first engagement means adapted to retain the first pair of wings about the head of a patient and second engagement means adapted to retain the said second pair of wings about at least one of the thoracic and lumbar regions of patient, the splint device being characterized in that the central support portion includes a part connected to the first pair of wings and a part connected to the second pair of wings, with each of the parts formed integrally with the connected pair of wings from a synthetic plastic material and having a longitudinal cavity and including within the cavity a plurality of longitudinal and diagonal stiffening ribs adapted to render the central support portion substantially inflexible laterally along its length.

* * * * *